United States Patent [19]

Suarato et al.

[11] Patent Number: 4,477,444
[45] Date of Patent: Oct. 16, 1984

[54] ANTRACYCLINE GLYCOSIDES, PHARMACEUTICAL COMPOSITIONS AND METHOD OF USE

[75] Inventors: Antonino Suarato; Sergio Penco, both of Milan; Federico Arcamone, Nerviano, all of Italy

[73] Assignee: Farmitalia Carlo Erba S.p.A., Milan, Italy

[21] Appl. No.: 434,509

[22] Filed: Oct. 15, 1982

Related U.S. Application Data

[63] Continuation-in-part of Ser. No. 336,705, Jan. 4, 1982, abandoned.

[30] Foreign Application Priority Data

Jan. 21, 1981 [GB] United Kingdom ............... 81 01792

[51] Int. Cl.$^3$ ....................... A61K 31/70; C07H 15/24
[52] U.S. Cl. ........................................ 424/180; 536/6.4
[58] Field of Search ......................... 424/180; 536/6.4

[56] References Cited

U.S. PATENT DOCUMENTS 4,067,969  1/1978  Penco et al. ................ 536/6.4
4,345,068  8/1982  Suarato et al. .............. 536/6.4
4,345,070  8/1982  Suarato et al. .............. 536/6.4

FOREIGN PATENT DOCUMENTS 48967  4/1982  European Pat. Off. ............. 536/6.4

Primary Examiner—Johnnie R. Brown
Attorney, Agent, or Firm—Oblon, Fisher, Spivak, McClelland & Maier

[57] ABSTRACT

Disclosed is a process for preparing the new antitumor glycosides: 4'-deoxy-3'-epi-daunorubicin and 4'-deoxy-3'-epi-doxorubicin starting from the known 3'-epi-4'-keto-N-trifluoroacetyl-daunorubicin.

Reduction of the 4'-keto group with sodium borohydride to the corresponding 4'-hydroxy group, reacting the so obtained intermediate with trifluoromethanesulphonic anhydride followed by treatment with n-tetrabutylammonium iodide, dehalogenated reductively, by treatment with tributyl tin hydride to 4'-deoxy-3'-epi-N-trifluoroacetyl-daunorubicin.

A mild alkaline hydrolysis removes the N-protecting group to give 4'-deoxy-3'-epi-daunorubicin which is successively transformed, via its 14-bromo derivative, in its doxorubicin analogue.

6 Claims, No Drawings

ANTRACYCLINE GLYCOSIDES, PHARMACEUTICAL COMPOSITIONS AND METHOD OF USE

CROSS REFERENCE TO RELATED APPLICATIONS

This application is a continuation-in-part of U.S. application Ser. No. 336,705 filed Jan. 4, 1982, now abandoned.

BACKGROUND OF THE INVENTION

Field of the Invention

The invention relates to anthracycline glycosides having antitumour properties, to processes for their preparation, and to pharmaceutical compositions containing them.

The invention provides 4'-deoxy-3'-epi-daunorubicin, 4'-deoxy-3'-epi-doxorubicin and their pharmaceutically acceptable salts.

4'-deoxy-3'-epi-daunorubicin and 4'-deoxy-3'-epi-doxorubicin have the following formula A:

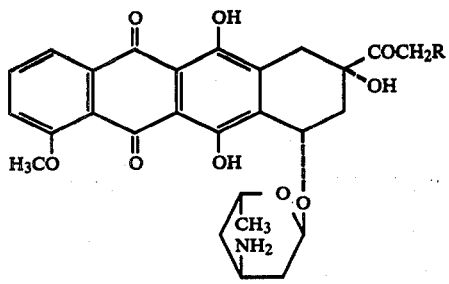

R representing a hydrogen atom and a hydroxy group respectively.

The invention further provides a process for the preparation of 4'-deoxy-3'-epi-daunorubicin, which process comprises reducing 3'-epi-4'-keto-N-trifluoroacetyl-daunorubicin (I) with sodium borohydride to obtain a mixture of axial II and equatorial III, 4' hydroxy derivatives replacing the 4'-hydroxy group of either of both thereof by an iodine atom by treatment with trifluoromethane-sulphonic anhydride in the presence of an organic base followed by treatment with an excess of tetrabutylammonium iodide, reductively dehalogenating the resultant 4'-iodo derivatives IV and V by treatment with tributyltin hydride in the presence of N,N'-azobis (isobutyronitrile), and removing the N-trifluoroacetyl group from the resultant 3'-epi-4'-deoxy-N-trifluoroacetyl-daunorubicin (VI) by mild alkaline hydrolysis.

The process is illustrated by the following reaction scheme, to which the compound numbers included in the last preceding paragraph refer. In the reaction scheme, D represents the group

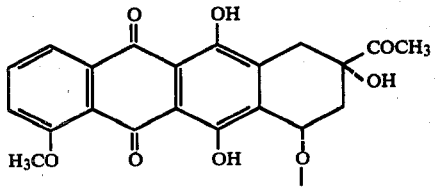

Me represents a methyl group and TFA represents a trifluoroacetyl group.

REACTION SCHEME

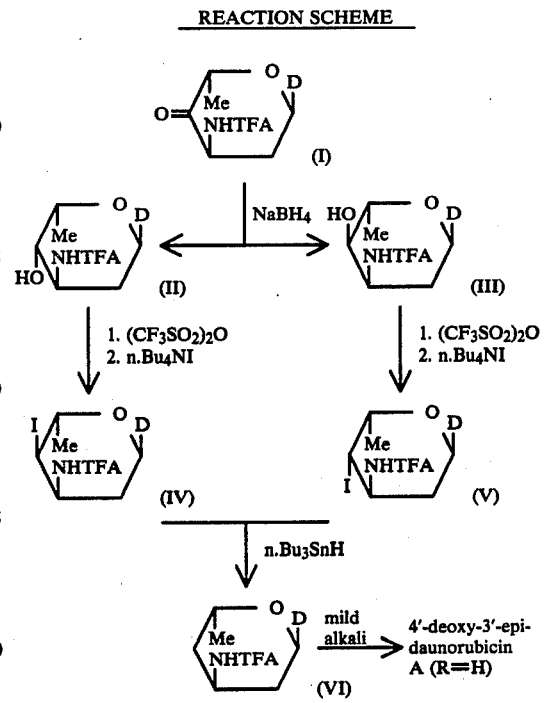

In order to introduce a halogen atom at the c-4' position of (II) and (III) via $SN_2$ displacement, the trifluoromethyl sulphonyloxy group is employed as leaving group. The trifluoromethylsulphonyl derivative allows the displacement to be carried out in mild conditions so as not to affect the glycosidic linkage. The introduction of the trifluoromethylsulphonyl group at the C-4' position of (II) and (III) is performed using trifluoromethylsulphonic anhydride. The organic base is suitably pyridine, and the reaction may be carried out at 0° C. The corresponding trifluoromethylsulphonates on treatment with an excess of tetrabutylammonium iodide are promptly converted in high yield to the iododerivatives (IV) and (V).

The 4'-deoxy-3'-epi-daunorubicin may be isolated as such or as one of its addition salts after suitable workup procedures. 4'-deoxy-3'-epi-daunorubicin may be converted to 4'-deoxy-3'-epi-doxorubicin by bromination and treatment of the resultant 14-bromo derivative with aqueous sodium formate in accordance with the method described in U.S. Pat. No. 3,803,124, and this conversion is within the scope of the invention.

The invention also provides a pharmaceutical composition comprising 4'-deoxy-3'-epi-daunorubicin, 4'-deoxy-3'-epi-doxorubicin or a pharmaceutically acceptable salt of either thereof in admixture with a pharmaceutically acceptable diluent or carrier.

The starting material, 3'-epi-4'-keto-N-trifluoroacetyl-daunorubicin (I), may be prepared from N-trifluoroacetyl-daunorubicin by treatment thereof with activated dimethylsulphoxide in a basic solvent. The activated dimethylsulphoxide is known (see K. Omura & D. Swern, Tetrahedron 1978 34, 1651–1660). Trifluoroacetic anhydride is the preferred activating agent. The reagent is suitably prepared in anhydrous methylene dichloride at from −50° C. to −70° C. The nature of the basic solvent affects the course of the reaction. For example, a bulky base such as 1,5-diazodicyclo (4,3,0)-non-5-ene (DBN) leads to 4′-keto-N-trifluoroacetyl-daunorubicin whereas the use of triethylamine affects the asymmertic C-3′ carbon atom giving a mixxture of epimeric ketones at the C-3′-position, namely 4′-keto-N-trifluoroacetyl-daunorubicin and 3′-epi-4′-keto-N-trifluoroacetyl daunorubicin in the approximate ratio 1:1. The 4′-keto-N-trifluoroacetyl-daunorubicin obtained using DBN as the basic solvent can also be epimerised to give an approximately 1:1 mixture of 4′-keto-N-trifluoroacetyl-daunorubicin and 3′-epi-4′-keto-N-trifluoroacetyl-daunorubicin by filtration over silica gel buffered to pH 7 with phosphate buffer.

The invention is illustrated by the following Examples. EXAMPLE 1

Preparation of 3′-epi-N-trifluoroacetyl-daunorubicin (II) and 3′,4′-diepi-N-trifluoroacetyl-daunorubicin (III)

A solution of 5 g (8.05 mmol) of 3′-epi-4′-keto-N-trifluoroacetyl-daunorubicin (I) in 500 ml of acetone was treated at room temperature with 0.4 g(10 mmol) of sodium borohydride dissolved in 200 ml of methanol. After five minuted the reduction was complete. The reaction mixture was then neutralized with 0.1 N aqueous hydrochloric acid, evaporated to a small volume (50 ml) under vaccum and diluted with 250 ml of methylene dichloride. The organic solution, washed with water was dried over anhydrous sodium sulphate and evaporated to dryness. The residue, containing a mixture of (II) and (III) approximately in the ratio 1:1, was chromatopraphed on a column of silica gel eluting with methylene dichloride: acetone (97:3 by volume) to give 1.8 g of 3′,4′-diepi-N-trifluoroacetyl-daunorubicin (III) and 2.4 g of 3′-epi-N-trifluoroacetyl-daunorubicin (II).

EXAMPLE 2

Preparation of 4′-deoxy-3′-epi-4′-iodo-N-trifluoroacetyl-daunorubicin (V) and 4′-deoxy-4′-iodo-3′,4′-diepi-N-tirfluoroacetyl-daunorubicin (IV)

To a stirred solution of 5 g of 3′-epi-N-trifluoroacetyl-daunorubicin (II), prepared as dexcribed in Example 1, in 100 ml of anhydrous methylene dichloride and 6 ml of anhydrous pyridine, cooled to 0° C., was added over a period of 10 minutes a solution of 2.07 ml of trifluoromethanesulphonic anhydride in 20 ml methylene dichloride. Then the organic phase was washed with a cooled 5% aqueous solution of sodium bicarbonate, water 0.1 N aqueous solution of hydrochloric acid and water in that order. The organic solution, dried over anhydrous sodium sulphate, was used in the following step without further purification. To the organic solution was added 10 g of tetrabutylammonium/iodide. After 1 hour at 40° C. the transformation was complete and the reaction mixture afforded (IV) in crude form. This was purified by chromatography on a column of silica gel using methylene dichloride as eluent to give 3.07 g of the iododerivative (IV) (yield 63%)FDMS [M+]:733. m.p. 142° C. TLC on Kiesel gel plate F254 (merck) using chloroform:acetone (9:1 by volume): Rf 0.42. 5 g of 3′,4′-diepi-N-trifluoroacetyl-daunorubicin (III) was converted to iododerivative (V) (4.46 g, yield 78.8%) as described for compound (III) FDMS [M+]:733. TLC on keisel gel plate F 254 (merck) using chloroform: acetone (9:1 by volume) : Rf 0.54 m.p. 144–148° C. (decomposition).

EXAMPLE 3

4′-deoxy-3′-epi-N-trifluoroacetyl-daunorubicin (VI)

A solution of 0.5 g of iododerivative (IV), prepared as described in Example 2, in 20 ml of anhydrous toluene at refluxing temperature was treated under stirring and a nitrogen atmosphere with 0.25 ml of tributyltin hydride and with 0.1 g of N,N′-azobis (isobutyronitrile). After 15 minutes the reduction was complete. The reaction mixture was cooled to room temperature and poured into an excess of petroleum ether (40° C.-60° C.). The precipitate was collected by filtration, washed with petroleum ether and dried under vacuum. 0.36 g of 4′-deoxy-3′-epi-N-trifluoroacetyl-daunorubicin (VI) were obtained (yield 87%). FDMS [M+]:607. m.p. 133°. TLC on kiesel gel plate F 254 (merck) using chloroform:acetone (9:1 by volume): RF 0.38. PMR (CDCL₃) inter alia: 1.22 (d. 3H, $\underline{CH_3}$—C—5′); 1.5–2.5 (m, 6H, $\underline{CH_2}$—C—2′, $\underline{CH_2}$—C—4′and $\underline{CH_2}$—C—8); 2.40 (s, 3H,$\underline{CH_3}$CO); 5.17 (m, $\underline{H}$—7); 5.48 (m, H—1′,W₁=5 hz). The iododerivative (V) was converted to (VI), as described for compound (IV).

EXAMPLE 4

4′-deoxy-3′-epi-daunorubicin (A; R=H)

A solution of 0.710 g of 4′-deoxy-3′-epi-N-trifluoroacetyl-daunorubicin, prepared as described in Example 3, in 10 ml of acetone was treated with 40 ml of a 0.1N aqueous solution of sodium hydroxide at 0° C. for 3 hours. Then to the solution was added 0.1 N aqueous hydrochloric acid to adjust the pH to 4.5 and the aglycones were eliminated by extractions with chloroform. Then the aqueous solution was adjusted to pH 8.6 and repeatedly extracted with chloroform. The combined extracts were dried over anhydrous sodium sulphate, concentrated to a small volume and acidified to pH 4.5 with 0.1 N methanolic hydrogen chloride to allow crystallization of the title compound as its hydrochloride: m.p. 188–189°0 C., [α]$_D^{20}$ +268° (c=0.05, methanol). TLC on Kiesel gel plate F 254 (Merck) using chloroform: methanol: water: acetic acid (80:20:7:3 by volume): Rf 0.85.

EXAMPLE 5

4′-deoxy-3′-epi-doxorubicin (A; R=OH)

A solution of 4′-deoxy-3′-epi-daunorubicin, prepared as described in Example 5, in a mixture of methanol and dioxan was treated with bromine to form the 14-bromoderivative. Treatment of the 14-bromoderivative with an aqueous solution of sodium formate gave 4′-deoxy-3′-epi-doxorubicin which was isolated as its hydrochloride. TLC. on Kiesel gel plate F 254 (Merck) using chloroform: Methanol: water: acetic acid (80:20:7:3: by volume): Rf=0.75

Biologic activity of 4′-deoxy-3′-epi-daunorubicin and 4′-deoxy-3′-epi-doxorubicin On Hela cells cloning efficiency in vitro, the new compounds 4′-deoxy-3′-epi-daunorubicin (henceforth XOO-0148) and 4′-deoxy-3′-epi-doxorubicin (henceforth XOO-0155) resulted less cytotoxic than daunorubicin and doxorubicin (Table 1). Against the P388 leukemia in mice, administered i.p. on day 1 after the tumor inoculation, both X00-0148 and XOO-0155 were less toxic and less potent than the corresponding parent compounds (Table 2)

At the maximal dose tested (30 mg/kg), XOO-0148 was not toxic and was about as active as daunorubicin at the maximal tolerated dose of 2.9 mg/kg; further studies will show whether it is possible to increase the dose achieving a higher antitumor efficacy than daunorubicin, without toxic effects.

The compound XOO-0155, at the maximal tolerated dose of 22.5 mg/kg exerted a remarkable antitumor effect, which was however lower than that observed after treatment with doxorubicin at the maximal tolerated dose of 10 mg/kg.

Compound XOO-0148 was also tested on the i.v. inoculated Gross leukemia. Mice were treated i.v. on day 1. Results reported in Table 3 show that XOO-0148 is less toxic than daunorubicin; at the maximal tolerated dose of 22.5 mg/kg. It was about as active as daunorubicin at the maximal tolerated dose of 6 mg/kg.

From these studies it can be concluded that XOO-0148 and XOO-0155 are endowed with remarkable antitumor activity.

TABLE 1

Activity on Hela cells cloning efficiency in vitro of XOO-0148 and XOO-0155
Treatment for 24 hours.

| Compound | Dose | % of controls | $ID_{50}$ (ng/m) |
|---|---|---|---|
| Daunorubicin* | 12.5 | 44,19 | 8 |
|  | 6.2 | 90,48 |  |
|  | 3.1 | 102,109 |  |
| XOO-0148* | 100 | 10 | 60 |
|  | 50 | 86 |  |
|  | 25 | 74,95 |  |
|  | 12.5 | 111 |  |
|  | 6.2 | 98 |  |
|  | 3.1 | 100 |  |
|  | 1.5 | 89 |  |
| Doxorubicin* | 25 | 26,22 | 15 |
|  | 12.5 | 63,93 |  |
|  | 6.2 | 88,111 |  |
|  | 3.1 | 82,104 |  |
| XOO-155* | 100 | 12,5 | 50 |
|  | 25 | 86,111 |  |
|  | 6.2 | 70,105 |  |

*Data of 2 experiments

TABLE 2

Activity against P388 ascitic leukemia of XOO-0148 and XOO-0155
Treatment i.p. on day 1 after tumor inoculation

| Compound | Dose mg/kg | T/C %[a] | Toxicity Death |
|---|---|---|---|
| Daunorubicin | 2.9 | 155 | 0/10 |
|  | 4.4 | 160 | 2/10 |
|  | 6.6 | 150 | 5/10 |
| XOO-0148 | 5.1 | 110 | 0/10 |
|  | 9.2 | 120 | 0/10 |
|  | 16.6 | 130 | 0/10 |
|  | 30 | 145 | 0/10 |
| Doxorubicin | 4.4 | 245 | 0/10 |
|  | 6.6 | 255 | 0/10 |
| XOO-0155 | 10 | 345 | 0/10 |
|  | 15 | 195 | 0/10 |
|  | 22.5 | 235 | 0.10 |
|  | 33.7 | 260 | 4/10 |
|  | 50 | 60 | 8/10 |

[a]T/C % = median survival time of treated mice/median survival time of controls X100

TABLE 3

Activity against Gross leukemia of XOO-0148
Treatment i.v. on day 1 after tumor inoculation

| Compound | Dose mg/kg | T/C %[a] | Toxicity Death |
|---|---|---|---|
| Daunorubicin | 4.6 | 180 | 0/10 |
|  | 6 | 250 | 0/10 |
|  | 7.8 | 250 | 3/10 |
| XOO-0148 | 22.5 | 240 | 0/10 |
|  | 33.7 | 150 | 6/10 |
|  | 50 | 120 | 10/10 |

[a]T/C % = median survival time of treated mice/median survival time of controls X100

What is claimed as new and desired to be secured by Letters Patent of the United States is:

1. An anthracycline glycoside of general formula A:

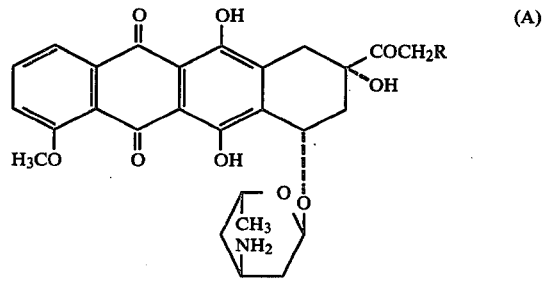

Wherein R is a hydrogen atom or a hydroxy group and its pharmaceutically acceptable salts.

2. A compound according to claim 1 which is 4'-deoxy-3'-epi-daunorubicin.

3. A compound according to claim 1 which is 4'-deoxy-3'-epi-doxorubicin.

4. An antitumoral pharmaceutical composition comprising a therapeutically effective amount of the glycoside of claim 1 in admixture with a pharmaceutically acceptable diluent or carrier.

5. A method of inhibiting the growth of a tumor selected from the group consisting of P388 ascitic leukemia and transplanted Gross leukemia, which comprises administering to a host afflicted with said tumor an amount of a compound according to claim 1 sufficient fo inhibit the growth of said tumor.

6. A method according to claim 5, wherein said compound is administered intraperitoneally or intravenously.

* * * * *